(12) United States Patent
Kishida et al.

(10) Patent No.: US 6,324,420 B1
(45) Date of Patent: *Nov. 27, 2001

(54) BLOOD VESSEL TRACKING APPARATUS (75) Inventors: Nobuyoshi Kishida, Utsunomiya; Yasuyuki Numajiri, Kawasaki; Toshiaki Okumura, Tokyo; Tomoyuki Iwanaga, Yokohama, all of (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/053,743

(22) Filed: Apr. 2, 1998

(30) Foreign Application Priority Data

Apr. 2, 1997 (JP) .................................................. 9-099647

(51) Int. Cl.$^7$ ........................................................ A61B 3/10
(52) U.S. Cl. ........................ 600/479; 600/504; 351/206; 351/209; 351/221
(58) Field of Search ..................................... 351/205, 206, 351/209, 210, 221, 216; 600/479, 504

(56) References Cited

U.S. PATENT DOCUMENTS

| | | | |
|---|---|---|---|
| 4,830,483 | 5/1989 | Kohayakawa et al. | 351/221 |
| 4,866,243 | 9/1989 | Sakane et al. | 219/121.62 |
| 5,129,400 | * 7/1992 | Makino et al. | 600/479 |
| 5,270,749 | 12/1993 | Okumura | 351/211 |
| 5,500,696 | 3/1996 | Masuda et al. | 351/205 |
| 5,630,179 | 5/1997 | Kishida | 396/18 |
| 5,751,396 | 5/1998 | Masuda et al. | 351/221 |
| 5,844,658 | * 12/1998 | Kishida et al. | 351/206 |
| 5,976,096 | * 11/1999 | Shimizu et al. | 600/479 |

* cited by examiner

Primary Examiner—Ruth S. Smith
(74) Attorney, Agent, or Firm—Fitzpatrick, Cella, Harper & Scinto (57) ABSTRACT

A blood vessel tracking apparatus includes a light source for emitting light and illuminating a blood-vessel with the light. The apparatus also includes a light-receiving sensor for receiving a blood vessel image made of light from the illumination light source reflected by the blood-vessel. The apparatus also includes an optical-path changing device for changing the optical-path of the light emitted from the illumination light source and a calculator for calculating the blood-vessel diameter of the illuminated blood-vessel based on an output of the light-receiving sensor, a plurality of times. A measuring device is also provided, which measures the change in blood-vessel diameter based on the calculating performed by calculating device.

16 Claims, 9 Drawing Sheets

FIG. 9A
BLINK

FIG. 9B
CALCULATE BLOOD VESSEL DIAMETER

FIG. 9C
RECORD BLOOD VESSEL DIAMETER

BLOOD VESSEL TRACKING APPARATUS

BACKGROUND OF THE INVENTION

1. Field of the Invention

The present invention relates to a fundus blood vessel monitoring or observing apparatus for measuring a blood-flow velocity or speed in the blood vessel in an eye fundus.

2. Description of the Related Art

Hitherto, there has been known a laser doppler fundus blood-flow meter or velocimeter as an apparatus for tracking of a blood vessel in an eye fundus. In the case of the fundus blood-flow meter, it is important that a blood vessel, through which a blood flow having a blood flow velocity to be measured flows, is selected, that the tracking of the selected blood vessel is performed, and that the selected blood vessel is irradiated, with measurement beams during the measurement of the blood flow velocity. Thus, there has been proposed a system which is provided with a detection mechanism for detecting a nictitation (or blink) of an eye to be examined. This system is adapted so that the tracking of the blood vessel is temporarily interrupted when nictitation of the eye occurs during the measurement of the blood flow velocity, and so that the tracking of the blood vessel is resumed by calculating a restart position when nictitation of the eye is finished and the system is brought into a condition in which the tracking thereof is enable to be performed. Further, there has been known another fundus blood-flow meter adapted so that the tracking of a blood vessel ceases when detecting an abnormality in a value represented by a tracking-position signal.

However, the aforementioned conventional system that is adapted to interrupt the tracking of a blood vessel has the drawback that, when resuming the tracking thereof, it cannot determine whether or not the tracking is performed on the same blood vessel as before the interruption of the tracking. Further, the blood flow meter adapted to detect an abnormality in a tracking-position signal has the following defect. Namely, in the case where another (adjacent) blood vessel is present in the vicinity of a blood vessel on which the tracking is performed, according to the conditions of eyelashes, tears, and fixation (of an eye), no abnormality is detected in the tracking position signal, so that it is erroneously determined that the measurement of a blood-flow velocity is normally finished.

SUMMARY OF THE INVENTION

The present invention aims at eliminating the aforementioned drawback and defect of the conventional art.

To achieve the foregoing object, in accordance with the present invention, there is provided an eye fundus blood-vessel observing apparatus having tracking means for performing tracking of a blood vessel in an eye fundus, which further comprises: blood-vessel image recording means for recording images of a plurality of blood vessels in an eye fundus obtained during tracking; blood-vessel-diameter calculating means for calculating blood-vessel diameters from the images of the aforesaid plurality of blood vessels; blood-vessel-diameter recording means for recording the calculated blood-vessel diameters; and computing means for computing a variation in the plural calculated blood vessel diameters.

Accordance to one aspect, the present invention relates to a blood-vessel tracking apparatus comprising an illumination light source for emitting light and illuminating a blood vessel with the light; a light-receiving sensor for receiving a blood-vessel image comprising light from the illumination light source reflected by the blood vessel, optical-path changing means for changing an optical path of the light emitted from the illumination light source, calculation means for calculating the blood-vessel diameter of the illuminated blood vessel based on an output of the light-receiving sensor, a plurality of times, and measurement means for measuring a change in blood vessel diameter based on the calculating performed by the calculating means. The apparatus can also comprise comparison means for comparing the change in blood vessel diameter, obtained by the measuring means, with a predetermined value. In addition, the apparatus can also comprise display means for displaying a result of the comparison made by the comparison means. Further, the device can include a detection sensor for detecting a nictitation of an eye to be examined. The calculation means in this embodiment calculates the blood vessel diameter before the nictitation detected by the detection sensor is performed and calculates the blood vessel diameter after the nictitation detected by the detection sensor is performed.

BRIEF DESCRIPTION OF THE DRAWINGS

Other features, objects and advantages of the present invention will become apparent from the following description of preferred embodiments with reference to the drawings in which like reference characters designate like or corresponding parts throughout several views, and in which:

FIG. 1 shows the relationship between FIGS. 1A and 1B and FIGS. 1A and 1B are schematic block diagrams showing the configuration of a first embodiment of the present invention;

FIG. 8 shows the relationship between FIGS. 8A and 8B and FIGS. 8A and 8B are schematic block diagrams showing the configuration of a second embodiment of the present invention.

DESCRIPTION OF THE PREFERRED EMBODIMENT

Hereinafter, the preferred embodiments of the present invention will be described in detail by referring to the accompanying drawings.

Figures 1, 1A:
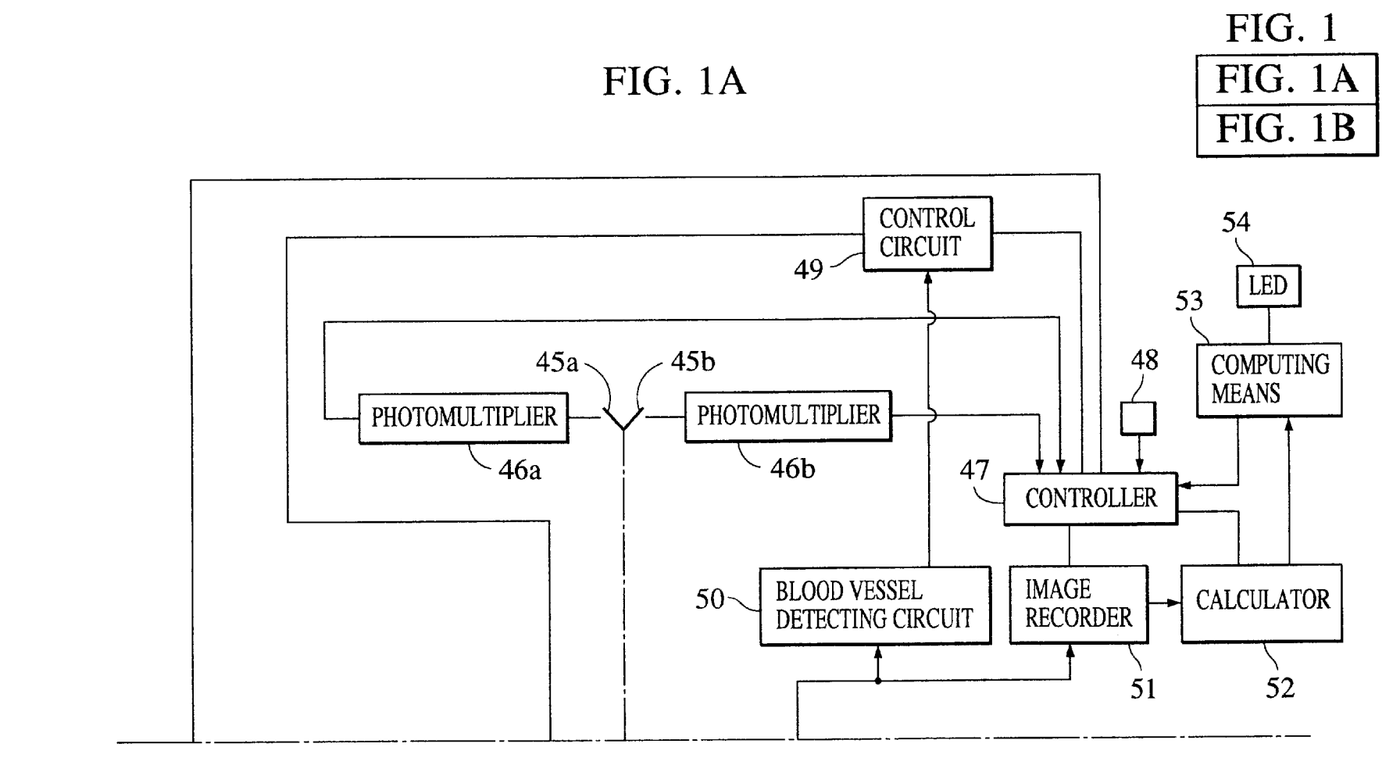
Figure 1B:
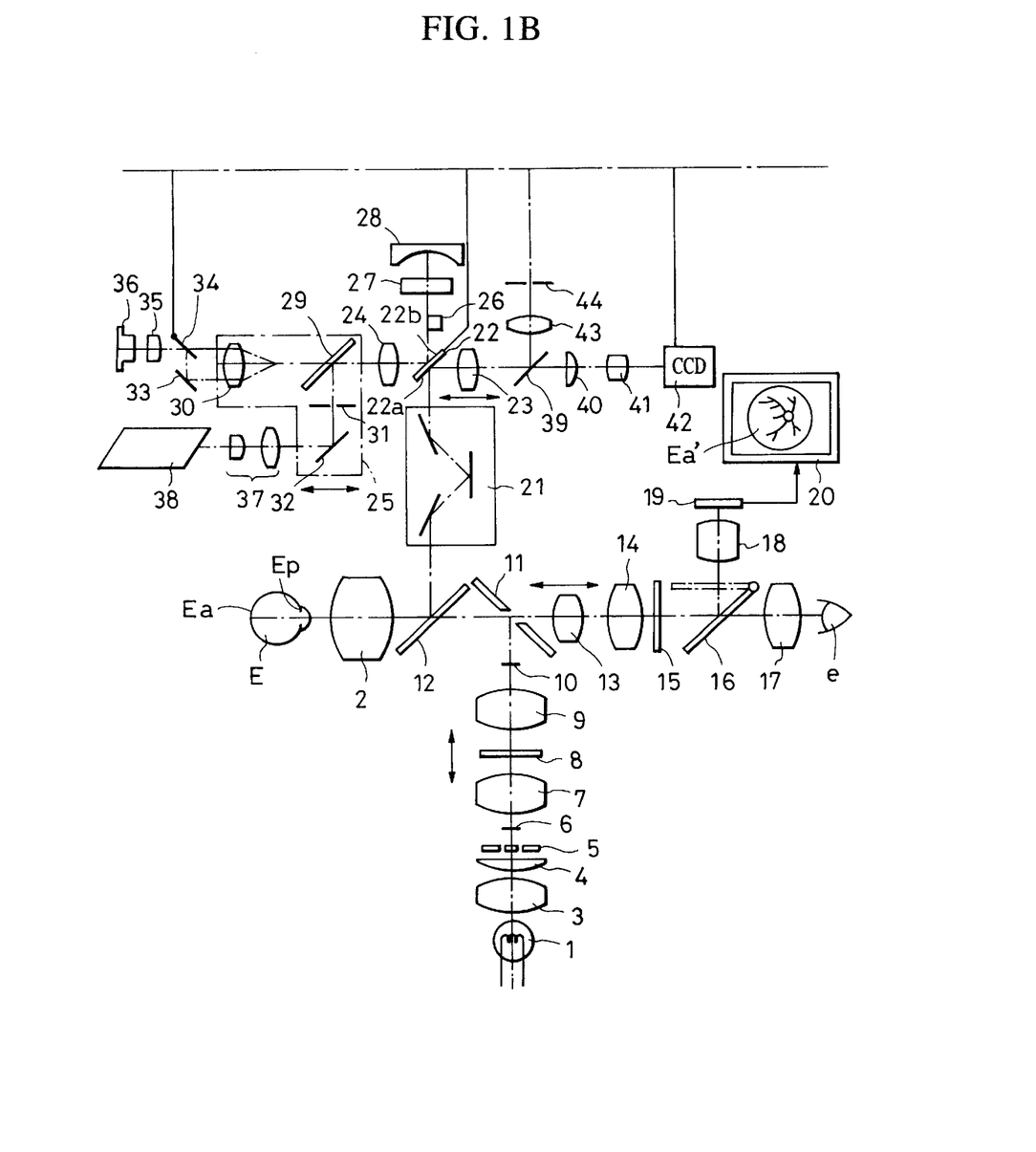

FIGS. 1A and 1B are diagrams showing the configuration of an eye-fundus, blood-flow meter which is the first embodiment of the present invention. A condenser lens 3, a field lens 4, which is provided with a band-pass filter for transmitting only light having wavelengths of, for instance, a yellow range, a ring slit 5 provided at a place which is nearly conjugate with the pupil $E_p$ of the eye E, a light-shielding member 6 provided at a place which is almost conjugate with a lens of the eye E, a relay lens 7, a transmission-type liquid crystal plate 8, which can move along the optical path and is a device for displaying a fixation mark, a relay lens 9, a light shielding member 10, which is provided in such a manner as to be almost conjugate with a portion in the vicinity of a cornea of the eye E, a perforated mirror 11, and a band-pass mirror 12 for transmitting light having a wavelength of a yellow region, are disposed in this sequence on an illumination optical path from an observation light source 1, which is constituted by a tungsten lamp emitting white light, to an objective lens 2 facing an eye E to be examined or tested. Thus, an illumination optical system is configured.

Incidentally, the ring slit 5 and the light shielding members 6 and 10 are used for separating eye-fundus illuminating light from eye-fundus observing light at an anterior ocular segment of the eye E. The shapes of these members 5, 6 and 10 do not matter as long as these members 5, 6 and 10 form a necessary light-shielding region.

An eye fundus observing optical system is configured to the rear of the perforated mirror 11. Namely, a focusing lens 13, which is movable along an observation optical path, a relay lens 14, a scale plate 15, an optical path changing mirror 16, which can be inserted into the observation optical path and removed therefrom, and an ocular lens 17 are arranged in this sequence along the observation optical path. Thus, the eye fundus observing optical system extends from mirror 11 to an eye e of a tester. When the optical-path changing mirror 16 is inserted into the observation optical path, what is called a television relay lens 18 and a CCD camera 19 are placed on a part, in a reflecting direction, in which light is reflected by a blood vessel, of the observation optical path. Further, an output of CCD camera 19 is connected to a liquid crystal monitor 20.

An image rotator 21 and a double-side polished galvanometric mirror 22, having an axis of rotation perpendicular to the plane of the drawing sheet of this figure, are placed on a part of an optical path extending in the reflecting direction of the band-pass mirror 12. A second focusing lens 23 is placed in the reflecting direction of the bottom-side reflection surface of the galvanometric mirror 22. Further, a lens 24 and a focusing unit 25, which is movable along an optical path in the reflecting direction of the top-side reflection surface of mirror 22, are placed in the reflecting direction of the top-side reflection surface of the galvanometric mirror 22. Incidentally, a front focal plane of the blood flow meter is conjugate with the pupil $E_p$ of the eye E, and the galvanometric mirror 22 is placed on this focal plane.

Moreover, an optical-path-length compensating semicircular plate 26, a black point plate 27 having a light-shielding portion and a concave mirror 28 are placed above the galvanometric mirror 22 and compose a relay optical system for leading a luminous flux, which is not reflected by the bottom-side reflection surface 22a of the galvanometric mirror 22 but passes therethrough, to the top surface 22b of the galvanometric mirror 22. Incidentally, the optical-path-length compensating semicircular plate 26 is used for compensating for the upward or downward shift of each of the top-side reflection surface 22b and the bottom-side reflection surface 22a of the galvanometric mirror 22, which is due to the mirror thickness thereof, as viewed in this figure, and acts thereon only in the optical path leading from mirror 22 to the image rotator 21.

In the focusing unit 25, a dichroic mirror 29 and a condenser lens 30 are disposed in this sequence on the same optical path as an optical path on which the lens 24 is placed. Further, a mask 31 and a mirror 32 are disposed in the reflecting direction of the mirror 29. This focusing unit 25 is adapted to move back and forth in the directions indicated by the arrow below unit 25, as one piece. Moreover, a stationary mirror 33 and an optical-path changing mirror 34, which can be retracted from the optical path from light source 36 to lens 30, are disposed in such a manner as to be in parallel with each other on the side of lens 30 from which the light is incident on the unit. Furthermore, the apparatus also indudes a collimator lens 35 and a semiconductor laser light source 36 for the blood-flow measurement, which is operative to emit, for example, coherent red light, in the incidence direction of the optical path changing mirror 34. Additionally, the apparatus comprises a beam expander 37, which consists of a cylindrical lens and optionally other lenses, and a tracking light source 38, which is operative to emit high-brightness green light differently from other light sources, in the incidence direction of beam expander 37 and mirror 32.

The aforementioned focusing lens 23, which is movable along a blood-vessel-detecting optical path along which light travels from source 36 to mirror 22 and to detector 42, a dichroic mirror 39, a field lens 40, a magnifying lens 41 and a detector comprising a one-dimensional CCD (charge coupled device) 42 provided with an image intensifier, are disposed in the reflecting direction of the bottom-side reflection surface 22a of the galvanometric mirror 22 and constitute a blood-vessel detecting system. Further, an imaging (or image formation) lens 43, a confocal diaphragm (or aperture) 44 and a pair of mirrors 45a and 45b, which are provided in such a way as to be almost conjugate with the pupil $E_p$ of the eye E, are provided in the reflecting direction of the dichroic mirror 39. Moreover, photo-multipliers 46a and 46b are disposed in the reflecting directions of the pair of mirrors 45a and 45b, respectively. Thus, a measurement-light receiving optical system is constituted in this manner.

Incidentally, for simplicity of drawing, all of the optical path s are shown on the same plane. However, the optical paths in the reflecting directions of the pair of mirrors 45a and 45b, the measurement optical path in the emitting direction, in which light is emitted, of the tracking light source 38 and the optical path extending from the semiconductor laser light source 36 to the mask 31 are perpendicular to the plane of the drawing sheet of this figure.

Further, the apparatus is provided with a system control portion 47 for controlling the entire apparatus. Input means operated by a tester, and outputs of the photo-multipliers 46a and 46b are connected to this system-control portion 47. Outputs of the system control portion 47 are connected to a control circuit 49 for controlling the galvanometric mirror 22, and to the optical-path changing mirror 34, respectively. Moreover, an output of the one-dimensional array CCD 42 is connected to the control circuit 49 through a blood-vessel-position detecting circuit 50.

In addition, an output of the one-dimensional array CCD 42 is connected to blood-vessel-image recording means 51 for recording images of a plurality of blood vessel in an eye fundus, which are obtained during the tracking of the blood vessels. Outputs of the blood vessel image recording means 51 are input into the system control portion 47 and blood-vessel-diameter calculating means 52 for calculating blood-vessel diameters from a plurality of blood-vessel images, respectively. Furthermore, outputs of the blood-vessel calculating means 52 are input into the system-control portion 47 and computing means 53 for computing a variation in blood-vessel diameter among the calculated blood-vessel diameters. Further, outputs of the computing means 53 are input into the system-control portion 47 and an LED 54 for the display of data.

White light emitted from the observation light source 1 passes through the condenser lens 3. Further, only light having wavelengths in a yellow region is transmitted by the field lens 4 provided with the bandpass filter. Then, the transmitted light further passes through the ring slit 5, the light-shielding member 6 and the relay lens 7. Subsequently, such light illuminates the transmission-type liquid crystal 8 from therebehind. Further, the light then passes through the relay lens 9 and the light-receiving member 10. Then, the light is reflected by the perforated mirror 11. Subsequently, only the light having wavelengths in a yellow region is transmitted by the band-pass mirror 12 and further passes through the objective lens 2. Then, a fundus illuminating-light luminous-flux image I is once formed from this light. Thereafter, such light illuminates the eye fundus Ea nearly uniformly.

At that time, a fixation mark is displayed on the transmission-type liquid crystal plate 8. Further, the fixation mark is projected onto the fundus Ea by the illuminating light. The image of the mark is presented to the eye E. Light reflected from the fundus Ea traces the same optical path and is taken out of the pupil $E_p$ as an eye-fundus, observation-light luminous flux. This light then passes through an opening formed in the central portion of the perforated mirror 11, the focusing lens 13 and the relay lens 14. Subsequently, an image of the fundus image Ea' is formed from this light on the scale plate 15. Thereafter, this light reaches the optical-path changing mirror 16. At that time, if the optical-path changing mirror 16 is retracted from the optical-path, the fundus image Ea' can be observed by the eye e through the ocular lens 17. In contrast, if the optical-path changing means 16 is inserted into the optical path, the fundus image Ea' formed on the scale plate 15 is formed again on the CCD camera 19 by the television relay lens 18. Further, this image is displayed on the liquid crystal monitor 20.

A tester performs the alignment of the apparatus by observing this fundus image Ea' by means of the liquid crystal monitor 20. At that time, it is preferable to select an observation method suited to his purpose. In the case of the observation method using the ocular lens 17, generally, the resolution and the sensitivity are higher than those of a method using the liquid crystal monitor 20. Thus, such an observation method is suitable for the case of diagnosing by reading a subtle change in the fundus Ea. In contrast, in the observation method using the liquid crystal monitor 20, the field of view is not limited, so that the fatigue of the tester is alleviated. Moreover, a change in part of the fundus image Ea' can be recorded electronically and sequentially by connecting outputs of the CCD camera 19 to an external video tape recorder or video printer. Therefore, this method is extremely effective in clinical diagnosis.

Next, the tester turns on the semiconductor laser light source 36 and the tracking light source 38. Measurement light emitted from the semiconductor laser light source 36 is collimated by a collimator lens 35. Further, in the case that the optical-path changing mirror 34 is inserted into the optical path from light source 36 to lens 30, the measurement light is reflected by each of the optical-path changing mirror 34 and the stationary mirror 33 and passes through a lower part of the condensing (or collective) lens 30. In contrast, in the case that the optical-path changing mirror 34 is retracted from the optical path, the measurement light passes through an upper part of the condensing lens 30 and the dichroic mirror 29. Then, an image is formed like a spot from this light by the condensing lens 30 on a place which is conjugate with the center of an opening of the mask 31.

Further, the beam diameter of tracking light emitted from the tracking light source 38 is magnified by the beam expander 37 by using a longitudinal magnification and a transverse magnification which are different from each other. Then, this light is reflected by the mirror 32. Thereafter, the image is shaped by the shaping mask 31. Subsequently, this light is reflected by the dichroic mirror 29 and moreover, is superimposed on the aforementioned measurement light. Light obtained by superimposing the measurement light upon the tracking light passes through the lens 24. Subsequently, the light obtained by the superimposing is once reflected by the upper reflection surface of the galvanometric mirror 22. Then, after this light passes through the black point plate 27, this light is reflected by the concave mirror 28 and further passes through the black point plate 27 and the optical-path length correcting semicircular plate 26 and is returned to the upper reflection surface of the mirror 22, where it passes therethrough to image rotator 21.

The concave mirror 28, the black point plate 27 and the optical-path-length correcting semicircular plate 26 are coaxially placed on the optical axis above the mirror 22. Further, the function of the relay system, namely, the function of forming images of the top and bottom surfaces of the galvanometric mirror 22 at a magnification of (−1) in collaboration with one another is imparted thereto. Therefore, measurement and tracking luminous fluxes reflected at the upper side of the galvanometric mirror 22 are put back to the notch-portion position of the galvanometric mirror 22 by the concave mirror 28. Thus, the luminous fluxes go to the image rotator 21 without being reflected by the galvanometric mirror 22. Further, both of the luminous fluxes are deflected to the objective lens 2 through the image rotator 21 and the band-pass mirror 12 and irradiate the fundus Ea through the objective lens 2.

In this way, the measurement light and the tracking light are reflected by the upper reflection surface of the galvanometric mirror 22. Further, when returned thereto, the measurement light and the tracking light are incident on the galvanometric mirror 22 in such a manner as to be off-centered from the optical axis of the objective lens 2. In this manner, the luminous fluxes scattered and reflected by the fundus Ea are condensed or collected by the objective lens 2 and are then reflected by the band-pass mirror 12. Subsequently, the luminous fluxes pass through the image rotator 21 and are reflected by the lower reflection-mirror surface 22a of the galvanometric mirror 22 and further pass through the focusing lens 23 to mirror 39. Finally, at the dichroic mirror 39, the measurement light is separated from the tracking light.

The tracking light is transmitted through the dichroic mirror 39. Then, an image is formed from this light on the one-dimensional CCD 42 as a magnified blood-vessel image, which is larger than the fundus image Ea formed by the fundus observation optical system, by the field lens 40 and the imaging lens 41. Further, data representing the amount of shift of the blood-vessel image is generated and outputted to the control circuit 49 on the basis of a blood-vessel image formed on the one-dimensional CCD 42. The control circuit 49 drives the galvanometric mirror 22 in such a way as to compensate for this amount of shift of the blood vessel image.

In contrast, the measurement light is reflected by the dichroic mirror 39 and passes through an opening in the confocal diaphragm 44 and is then reflected by the pair of mirrors 45a and 45b. The light reflected by each of the pair of mirrors 45a and 45b is received by a corresponding one of the photo-multipliers 46a and 46b, respectively. Further, output signals of the photo-multipliers 46a and 46b are outputted to the system-control portion 47. Moreover, a frequency analysis of the received output signals is performed in this control portion 47, so that the blood-flow velocity in the fundus Ea is obtained.

When starting the measurement of blood flow, the blood vessel in the fundus Ea, the tracking of a blood vessel in the fundus Ea, to which the apparatus is currently aligned, is performed. Then, the measurement of blood flow is conducted for a time period of 4 seconds. At that time, 250 blood vessel images appear on the one-dimensional CCD 42 per second. Further, every second, the first 25 images of the remaining blood vessels are recorded on the blood-vessel image recording means 51. Thus, for a time period of 4 seconds, 4×25=100 blood-vessel images are recorded thereon. Upon completion of the measurement for the time period of 4 seconds, data respectively representing such 100 blood-vessel images are converted by the blood-vessel-diameter calculating means 52 into data representing the blood-vessel diameters. Moreover, data representing the blood-vessel diameters obtained by the conversion is inputted to the computing means 53, whereupon variations in the blood-vessel diameter are calculated. If the mean (or average) value of such variations is, for example, not more than 10%, it can be considered that the tracking of one blood vessel is securely performed.

The tracking state is displayed on the displaying LED 54, which is operative to perform two-color (or dichroic) light emission. If tracking fails, the indication representing the tracking state is displayed in red. Conversely, if tracking is successful, the indication is displayed in blue. In the case of this embodiment, if the variation is not more than 10%, the tracking indication is displayed in blue. Furthermore, if the variation is more than 10%, the tracking indication is displayed in red. Incidentally, the data representing the variation may be indicated by using 7-segment LED or the like instead of the displaying LED 54.

Figure 2:
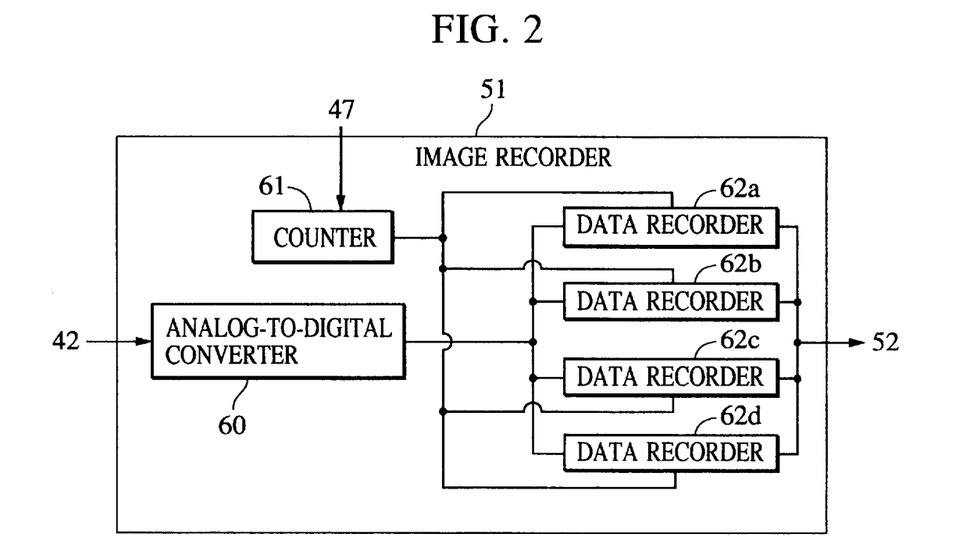
FIG. 2 is a schematic block diagram showing the configuration of a blood-vessel-image recording means.

FIG. 2 is a diagram showing the configuration of the blood-vessel recording means 51 which consists of A/D (analog-to-digital) conversion portion 60, a counting portion 61 and data-recording portions 62a to 62d. Output of the one-dimensional CCD 42 is connected to the A/D conversion portion 60. The output of the system-control portion 47 is connected to the counting portion 51. The output of the A/D conversion portion 60 and the counting portion 61 are connected to the data recording portions 62a to 62d.

The A/D conversion portion 60 is adapted to convert the blood-vessel image into digital data at all times. The initial value set in the counting portion 61 is "0". When starting the measurement of the blood flow, the value (or count) represented by the counting portion 61 is changed from "0" to "1". The data-recording portion 62a becomes active when the value indicated by the counting portion 61 is "1". Then, the data-recording portion 62a records data, which are sent from the A/D conversion portion 60, serially. After coming to indicate the value "1", (data indicated by) the counting portion 61 is incremented by 1 every second. Thus, the data-recording portion 62a records digital data within the recordable range or capacity thereof. In the case of this embodiment, such a recordable (or recording) capacity of the data recording portion 62a is set in such a manner as to correspond to data of 25 blood vessels. Thus, during the time the value indicated by the counting portion 61 is "1", the data of 25 blood vessels are recorded in the recording portion 62a. When the value indicated by the counting portion 61 is changed from "1" to "2", the blood-vessel images are recorded in the data-recording portion 62b. The data-recording portions 62c and 62d record data similarly as in the case of the portions 62a and 62b. Thus, when the counting portion 61 counts to "3", blood-vessel images are recorded in data recording portion 62C and when counting portion 61 counts to "4", blood-vessel images are recorded in data recording portion 62d.

Figure 3:
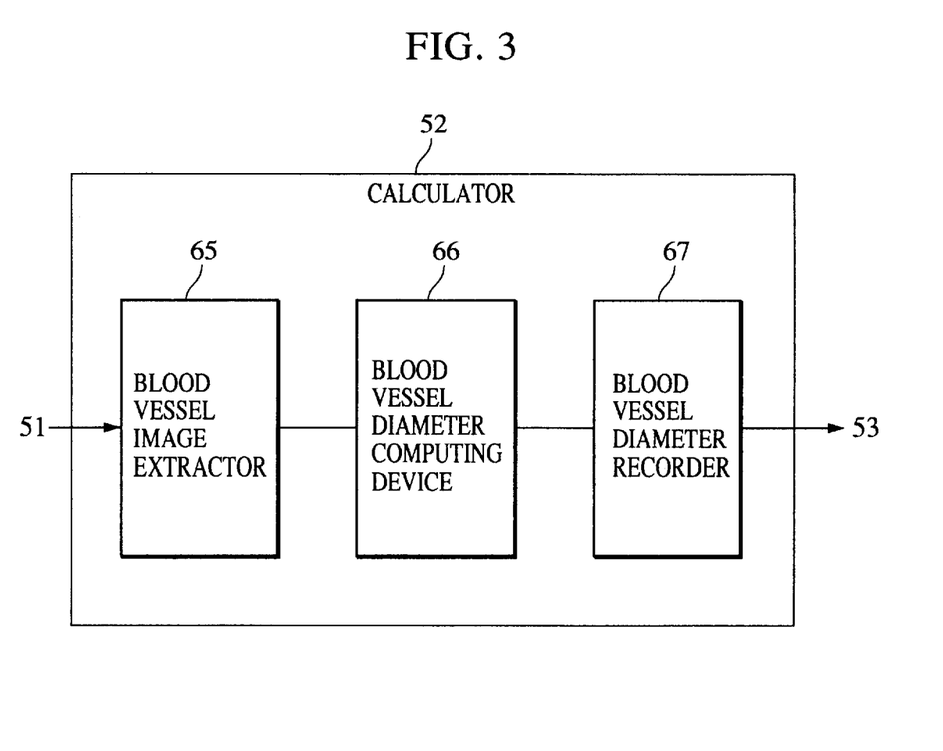
FIG. 3 is a block diagram showing the configuration of a blood-vessel-diameter calculating means.

FIG. 3 is a diagram showing the configuration of the blood-vessel-diameter calculating means 52 which is composed of a blood-vessel extraction portion 65, a blood-vessel-diameter computing portion 66 and a blood-vessel diameter data recording portion 67. The output of the blood-vessel-image recording means 51 is input into the blood-vessel extraction portion 65, the blood vessel diameter computing or calculating portion 66 and the blood-vessel-diameter data recording portion 67 in sequence. Thereafter, the output of the blood-vessel image recording means 51 is outputted to the computing means 53.

Figure 4:
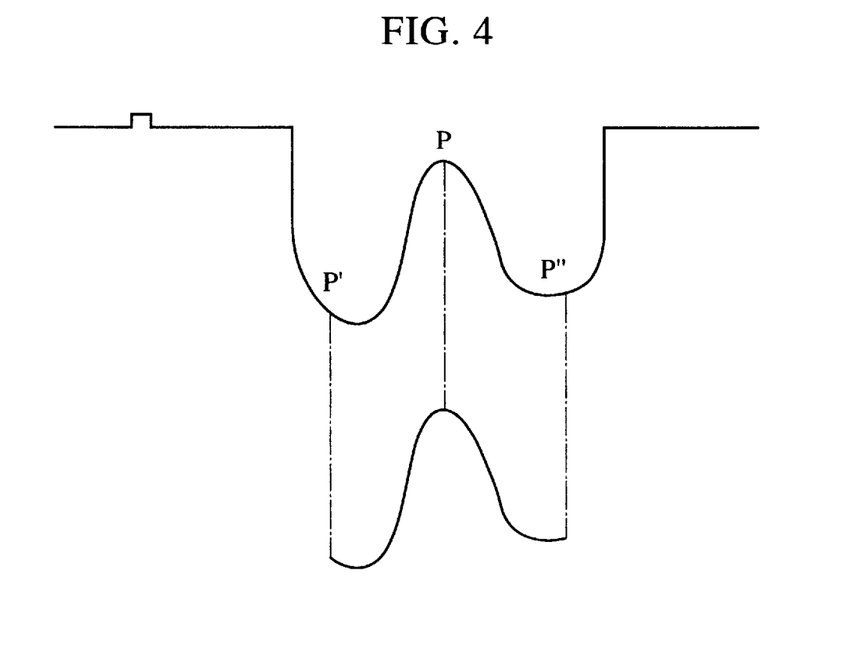
FIG. 4 is a schematic diagram illustrating a blood vessel extraction.

The blood-vessel extraction portion 65 is operative to extract the image of a blood vessel, which is placed at a tracking position, from the blood-vessel images recorded in the data recording portions 62a to 62d of the blood-vessel-image recording means 51. In this case, the tracking is set so that the scanning is performed around the central point P of the blood vessel shown in FIG. 4. Thus, the blood-vessel extraction portion 65 extracts images of blood vessel s from a range (P' to P") extending from the central point P toward the front and back end of the fundus, namely, the range in which the largest blood vessels are present. Further, data representing the images of blood vessel s extracted by the blood-vessel extraction portion 65 is inputted to the blood-vessel diameter calculating portion 66. Incidentally, the apparatus may employ a method of determining the tracking position by using synchronization pulses corresponding to output signals of the one-dimensional CCD 42, for example, and determining the tracking position as nth to m'th data by counting from data corresponding to the position of a synchronization pulse.

Figure 5:
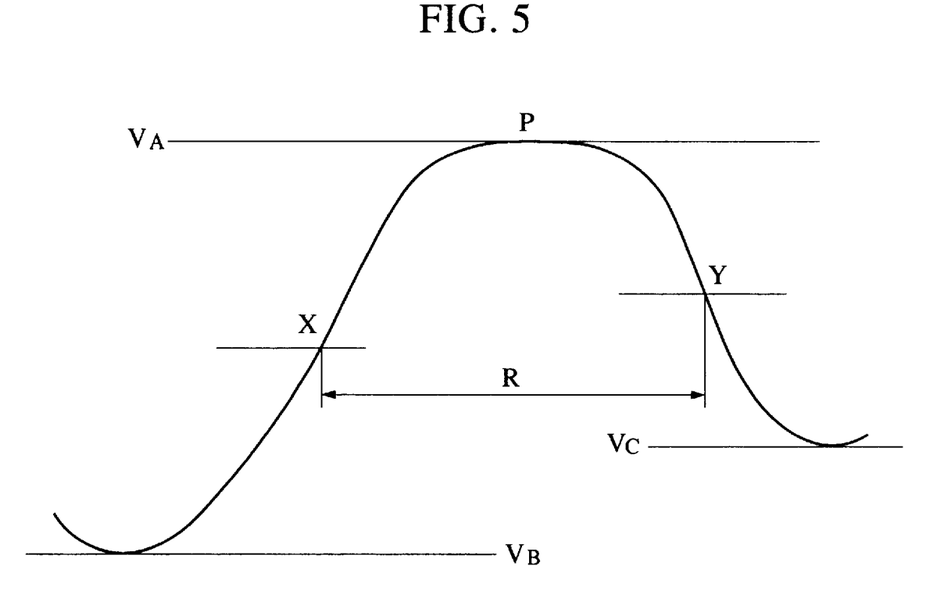
FIG. 5 is a diagram illustrating a blood-vessel image calculating portion.

The blood-vessel-diameter calculating portion 66 searches the blood-vessel images extracted as shown in FIG. 5 for inflection (or inflexion) points in the forward and backward directions (namely, the lateral directions as viewed in this figure) from the central point P and detects the levels $V_B$ and $V_C$ respectively corresponding to the inflection points. Let $V_A$ denote the level at the central point P. Then, the calculating portion 66 obtains the intersection (point) X of the intermediate (or middle) level between the levels $V_A$ and $V_B$ and the blood-vessel image, and the intersection Y of the intermediate level between the levels $V_A$ and $V_C$ and the blood-vessel image. Furthermore, the portion 66 calculates the width R between the intersection points X and Y as a blood-vessel diameter. The obtained blood vessel diameters are recorded in the blood-vessel, data recording portion 67 individually. A total of 100 values of the blood vessels are calculated therein.

Data representing the blood-vessel diameters recorded in the blood-vessel, data-recording portion 67 are sent to the computing means 53. Then, the mean value of 25 blood-vessel diameters of each set measured in one second is calculated by excluding the blood-vessel diameters of blood vessels located outside the aforementioned range. Thus, a total of 4 mean values are obtained from 100 blood-vessel diameters, namely, four sets of 25 blood-vessel diameters. Subsequently, a variation in the mean value of the blood-vessel diameters is calculated as the difference between the maximum value and the minimum value of the four mean values. Namely, in the case where it is supposed that the mean value is, for example, 100 or so, if the difference between the maximum value and the minimum value of the mean value is not more than 10, the apparatus determines that the tracking is in a good or successful state. In contrast, if the difference between the maximum value and the minimum value of the mean value is more than 10, the apparatus determines that the tracking is in a bad or failed state. Moreover, the tracking state is displayed on the displaying LED 54. Namely, the failed state of the tracking is indicated in red, while the successful state thereof is indicated in blue.

Figure 6:
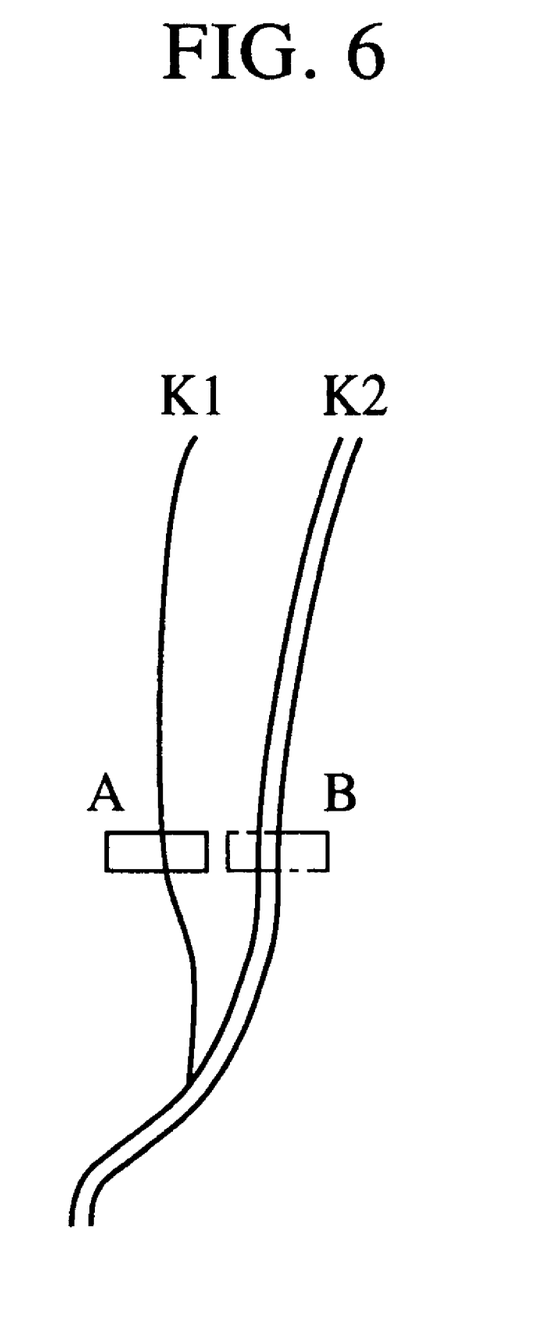
FIG. 6 is a diagram illustrating the tracking (of a blood vessel in an eye fundus)
Figure 7A:
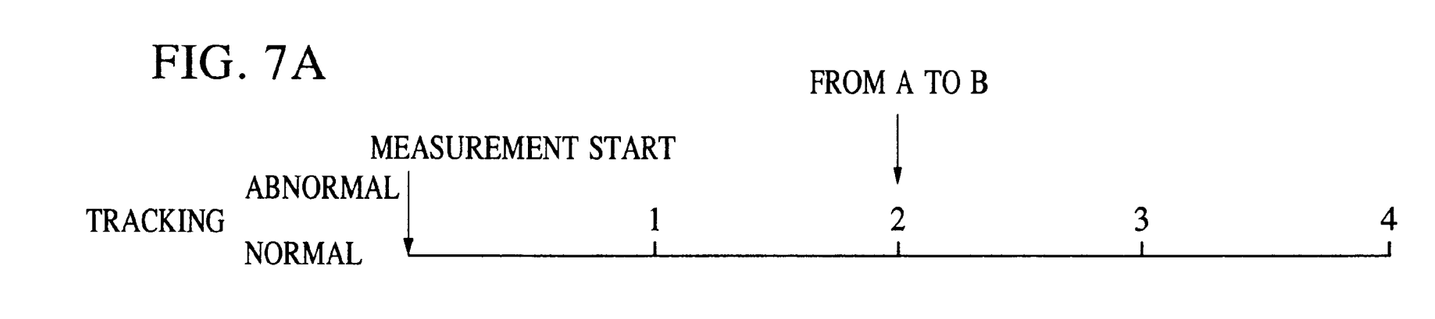
FIGS. 7A–7C are timing charts illustrating a measurement of a blood flow velocity.
Figure 7B:
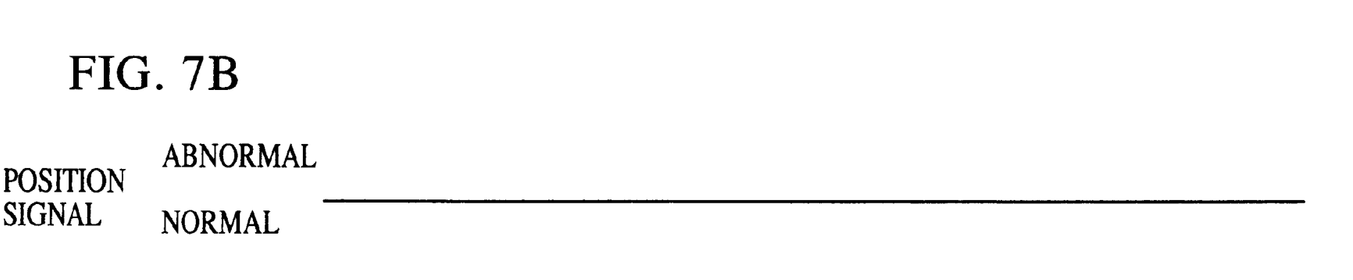
Figure 7C:
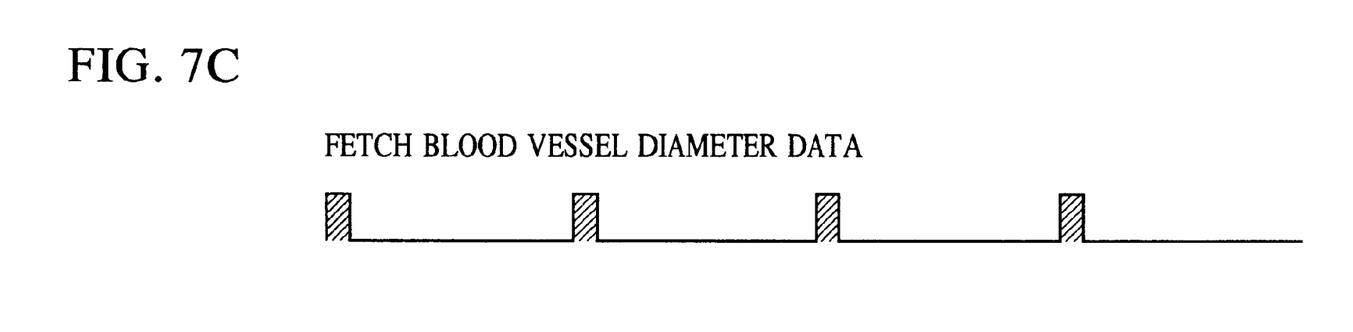

FIG. 6 is a diagram illustrating the state of the tracking of a blood vessel in an eye fundus. Measurement is performed for a time period of 4 seconds, and is started by performing the tracking of a blood vessel K1, which is to be measured, at the position A. After performing the measurement for a time period of 2 seconds, the tracking point is moved to an adjacent blood vessel K2 due to the influence of the fixation of the eye. Further, the tracking operation is continued at the tracking position B. FIGS. 7A–7C are timing charts illustrating such a process performed at that time. In this chart, FIG. 7A indicates the tracking state during the measurement; FIG. 7B indicates the tracking position signal (namely, this figure indicates that the position signal is normal during the operation which is performed for the time period of 4 seconds). However, there is the possibility that the blood-flow velocity in a first half period (namely, first two seconds), in which the tracking of the blood vessel K1 is performed, is different from the blood-flow velocity in a second half period (namely, a second two seconds), in which the tracking of the blood vessel K2 is performed. In the case of the conventional apparatus and method, which do not capture blood-vessel images, it is determined that such a measurement is normally finished. Thus, in the conventional apparatus and method, the difference in the blood-flow velocity is not detected.

In contrast, in the case of this embodiment, the blood-vessel recording means 51 is adapted to record the images of the first 25 blood vessel s of the remaining blood vessel s every one second. Namely, the recording of the blood vessels is performed, as illustrated in FIG. 7C. Upon completion of the measurement, data representing the blood-vessel diameters are obtained by the blood-vessel-diameter calculating means 52 and the computing means 53 from the blood-vessel images recorded in the blood-vessel-image recording means 51. Subsequently, the variation in the blood-vessel diameter is calculated from such blood-vessel-diameter data. At that time, as shown in FIG. 6, the relation between the width of the blood vessel K1 and the width of the blood vessel K2 is expressed almost as follows:

$$K2 \approx 2 \times K1$$

Thus, there is caused a variation of more than 10% among the diameters of the measured blood vessels. As a result, the red indication is displayed in the LED 54. In this manner, even if there is no abnormality in the tracking-position signal, the tester can know that the tracking is not performed normally.

Additionally, there may occur the case that the images of the blood vessel s undergoing the tracking are unstable owing to the influence of eyelashes or tears, and that a measurement beam (or light) does not accurately irradiate the blood vessel. In the case of this embodiment, the blood-vessel diameters are calculated from the blood-vessel images. Moreover, the variation in the blood-vessel diameter is computed. Thus, if the blood vessel images are unstable, the red indication is displayed in the LED 54. Conversely, if the blood-vessel images are stable, the blue indication is displayed therein. Consequently, the tester can know or discriminate the tracking state very easily.

Incidentally, in the case of this embodiment, it is determined on the basis of the calculation of the blood-vessel diameters from the plural blood-vessel images upon completion of the measurement whether or not the tracking of a blood vessel is performed securely. However, the apparatus may be adapted so that the blood-vessel diameters and the mean values are obtained in real time and that the measurement is stopped when detecting the movement or shift of the tracking point during the measurement.

Additionally, in the case of this embodiment, the tracking state is determined according to the variation in the mean value of the blood-vessel diameters obtained every second. However, the tracking state may be determined by utilizing statistic techniques, such as a standard deviation and a variance. Further, in the case of this embodiment, 10% is used as the threshold for the variation. However, the determination accuracy may be enhanced or degraded by changing such a threshold value.

In addition, in the case of this embodiment, the blood-vessel diameter at the time of initiating the measurement, and the blood-vessel diameters obtained correspondingly at each second are recorded in the apparatus. However, the apparatus may employ a method of making a comparison between the blood-vessel diameters at the measurement starting time and the measurement terminating time. Alternatively, the apparatus can adopt a method of making a comparison between the blood-vessel diameters at the measurement starting moment and another certain moment.

Figures 8, 8A:
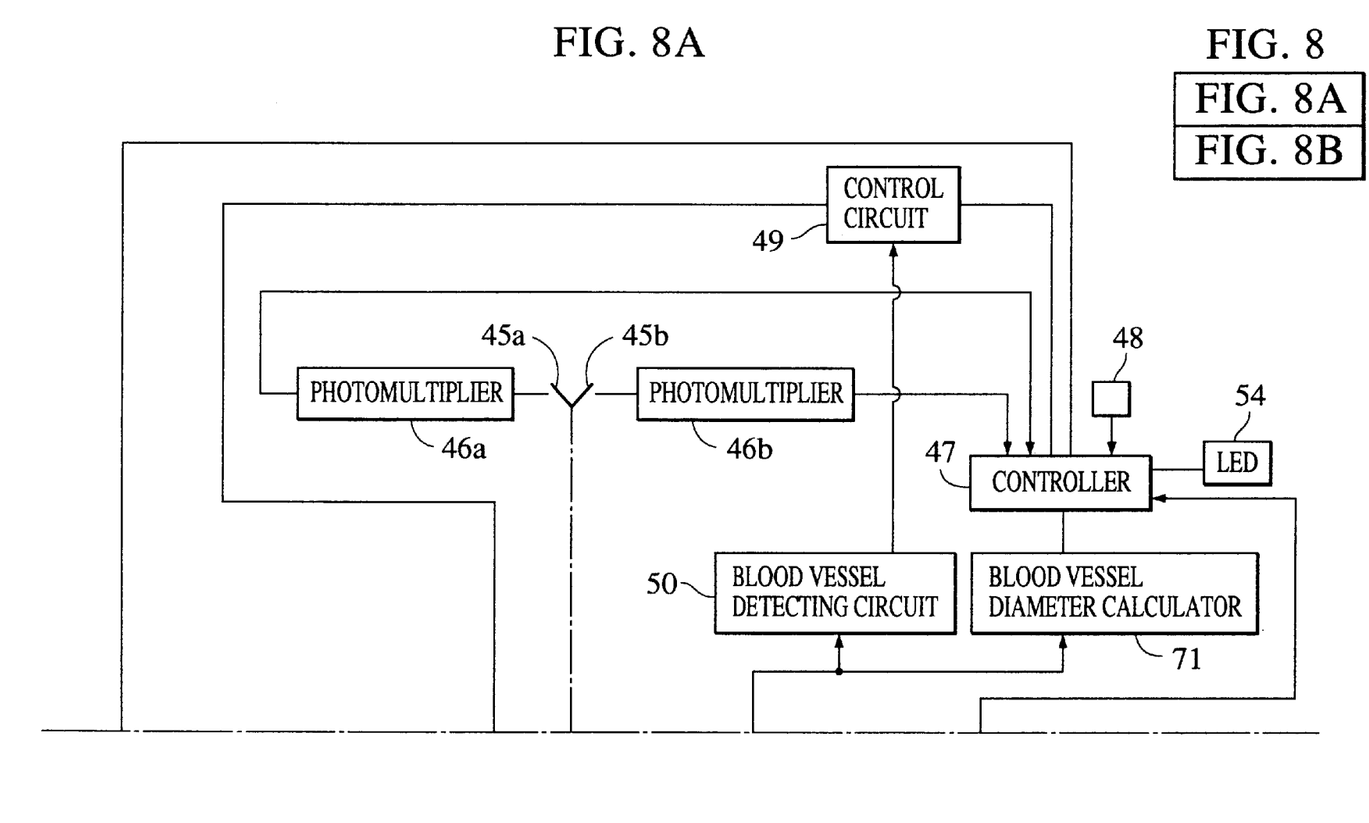
Figure 8B:
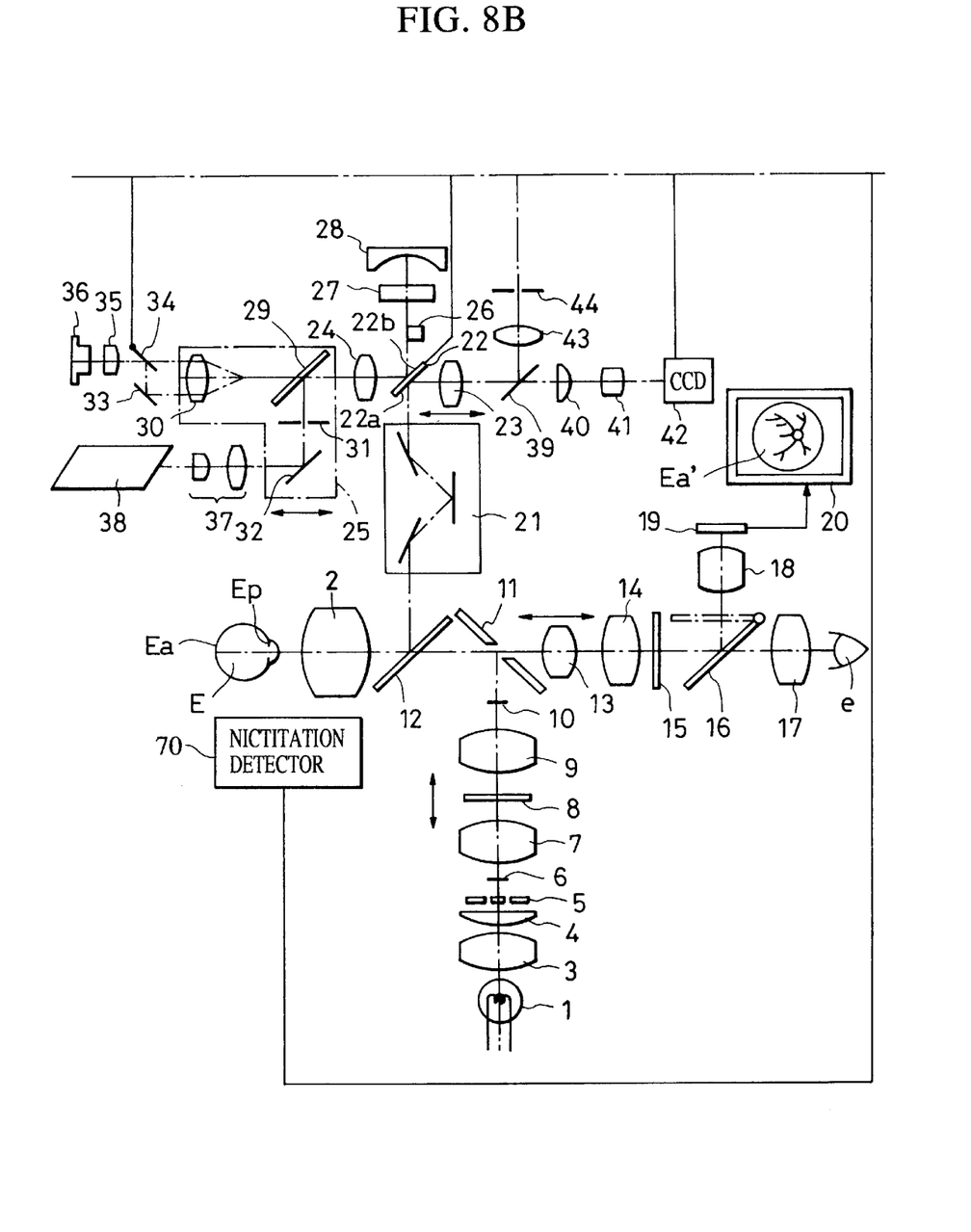

FIGS. 8A and 8B are diagrams showing the configuration of a second embodiment, namely, an eye-fundus, blood-flow meter provided with a nictitation detecting mechanism. As shown in this figure, the nictitation detecting mechanism 70 is provided in the vicinity of an objective lens 2, and an output of the nictitation detecting mechanism is connected to the system control portion 47. Moreover, an output signal of the one-dimensional CCD 42 is input into the blood-vessel-position detecting circuit 50 and is also connected to the blood-vessel-diameter calculating means 71. Furthermore, an output of the blood-vessel diameter calculating means 71 is connected to the system-control portion 47. The rest of the configuration of this embodiment is similar to the corresponding elements as illustrated in FIGS. 1 and 1B. Further, in FIGS. 8A and 8B, reference numerals identical to those in FIGS. 1A and 1B designate like members.

The nictitation detecting mechanism 70 is operative to output signals, which indicate the initiation and termination of a nictitation of the eye E, to the system control portion 47. The blood-vessel-diameter calculating means 71 is operative to convert the blood vessel images outputted from the one-dimensional CCD 42 to the data representing the blood-vessel-diameters. Furthermore, when receiving a blood vessel diameter starting signal from the system control portion 47, the blood-vessel-diameter calculating means 71 calculates the blood-vessel diameters and outputs the data representing the blood-vessel diameters to the system control portion 47.

Figure 9A:
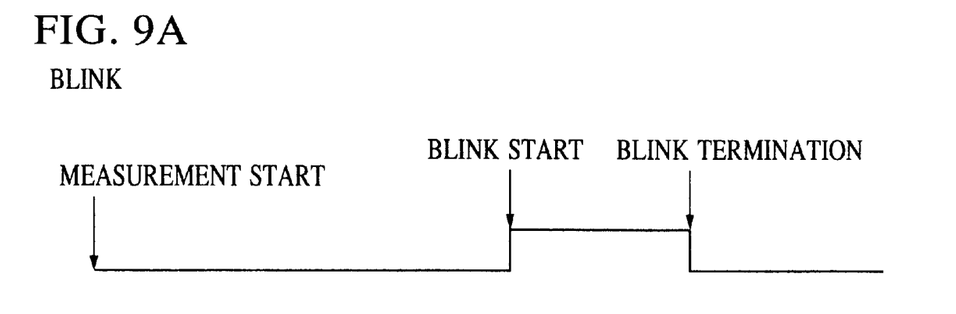
FIGS. 9A–9C are timing charts illustrating an operation of the second embodiment of the present invention in the case that a nictitation of an eye occurs.
Figure 9B:
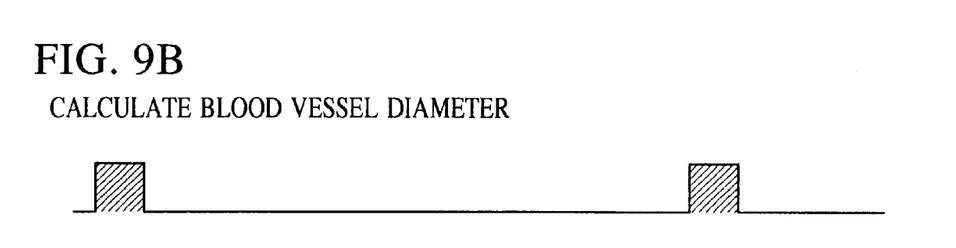
Figure 9C:
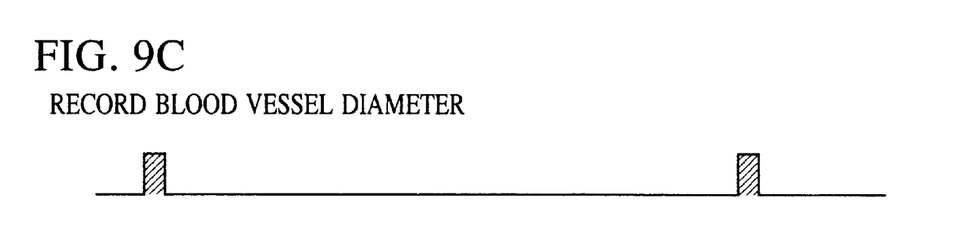

FIGS. 9A–9C are timing charts illustrating a blink (or nictitation) detecting operation. In this chart, FIG. 9A shows a blink starting signal and a blink terminating signal; FIG. 9B shows a signal for calculating a blood-vessel diameter at the time of starting the measurement and at the time of terminating the blink; and FIG. 9C shows a signal for recording the blood-vessel diameters at such times (or moments). The system-control portion 47 takes in the data representing the blood-vessel diameters from the blood-vessel calculating means 71 when commencing the blood-flow measurement, and further records the blood-vessel diameter at the time of commencing the blood-flow measurement. Further, if a blink terminating signal is inputted to the system control portion 47 after a blink (or nictitation) starting signal is inputted from the nictitation detecting mechanism 70 to the system-control portion 47, the system-control portion 47 takes in the data representing the blood vessel diameter from the blood-vessel-diameter calculating means 71, and further records the blood-vessel diameter at the time of terminating this blink.

Upon completion of the measurement, the system-control portion 47 compares the blood-vessel diameter at the time of starting the measurement with that at the time of terminating the measurement. As a result, if the difference between the blood-vessel diameter between the time of starting the measurement and the time of terminating the measurement is larger than, for example, 10%, the system-control portion 47 determines that the tracking has been performed on different blood vessels. In contrast, if it is not more than 10%, the portion 47 determines that the tracking is performed on the same blood vessel. Further, similarly as in the case of the first embodiment, in the case where the system control portion 47 determines that the tracking has been performed on different blood vessels, the red indication is displayed in the LED 54. Conversely, in the case where the system-control portion 47 determine that the tracking has been performed on the same blood vessel, the blue indication is displayed in the LED 54. In this way, after terminating the measurement, the tester knows whether or not the tracking is performed on the same blood vessel as at the time of starting the measurement. In the case of this embodiment, by making the comparison between the blood-vessel diameters respectively obtained at the time of starting the measurement and at the time of terminating the measurement, after the termination of the measurement, it is determined whether or not the tracking has been performed on the same blood vessel. However, the apparatus may be adapted so that the comparison between the blood-vessel diameters is performed during the measurement and that the measurement is stopped when detecting a change of the blood vessel on which the tracking is performed.

As above described, the fundus blood-vessel observing apparatus of the present invention records the fundus blood-vessel image at the time of starting the tracking to thereby determine on the basis of the recorded blood-vessel image at the time of starting the tracking whether or not the tracking is performed on the same blood vessel.

Further, the fundus blood-vessel observing apparatus of the present invention calculates the variation in the blood-vessel diameter obtained from plural blood-vessel images to thereby determine on the basis of the degree of the variation whether or not the tracking is performed on the same blood vessel.

Moreover, the fundus-blood-vessel observing apparatus of the present invention compares the blood-vessel diameter at the time of starting a blink with the blood-vessel diameter at the time of terminating the blink to thereby determine after terminating the blink whether or not the tracking is performed on the same blood vessel as the vessel on which the tracking is performed at the time of starting the blink.

What is claimed is:

1. A blood vessel tracking apparatus comprising:
    an illumination system, having a light source for illuminating a blood vessel of an eye to be examined with light;
    a sensor for receiving an image of the blood vessel illuminated with the light; and
    a processing system for calculating, based on an output of said sensor, a diameter of the illuminated blood vessel a plurality of times, in order to determine a change in blood vessel diameter, and wherein the processing system further determines whether the same blood vessel has been used for the calculating based on the change in blood vessel diameter.

2. The apparatus according to claim 1, wherein said processing system further executes processing for comparing the change in blood vessel diameter with a predetermined value.

3. The apparatus according to claim 2, further comprising a display for displaying a result of the comparison.

4. The apparatus according to claim 1, further comprising a detection system for detecting a nictitation of an eye, and said processing system calculates the blood vessel diameter before the detection of the nictitation and also calculates the blood vessel diameter after the detection of the nictitation.

5. A blood vessel tracking apparatus comprising:
    an illumination system, having a light source and a movable mirror, for illuminating a blood vessel of an eye to be examined with light;
    a sensor for receiving an image of the blood vessel illuminated with light; and
    a processing system for calculating, based on an output of said sensor and after a change of an optical path of the light effected by said movable mirror, a diameter of the illuminated blood vessel a plurality of times to produce a plurality of calculated blood-vessel diameters, and for calculating the variations in the calculated blood-vessel diameters, wherein said processing system also determines whether said movable mirror has performed successful tracking of the illuminated blood vessel in accordance with the calculated variations in the blood-vessel diameters.

6. A blood vessel tracking apparatus according to claim 5, wherein said processing system further executes processing for measuring a change in blood vessel diameter based on the calculation and for determining whether the same blood vessel has been used for calculating the blood vessel diameter based on the change in the measured blood vessel diameter.

7. A blood vessel tracking apparatus according to claims 1 or 6, wherein said processing system determines whether a single blood vessel was used by said apparatus when the change in blood vessel diameter changes by more than a predetermined amount.

8. A blood vessel tracking apparatus according to claims 1 or 6, wherein said processing system calculates a mean value for a plurality of sets of blood vessel diameters, calculates the difference between the maximum and minimum values of the mean values, and uses that difference in determining whether a single blood vessel was used by said processing system when the change in blood vessel diameter changes by more than a predetermined amount.

9. A blood vessel tracking apparatus according to claims 1 or 6, wherein said processing system determines whether the same blood vessel has been used when the difference in calculated blood vessel diameters is less than 10%.

10. A blood vessel tracking apparatus according to claim 5, further comprising a detection system for detecting a nictitation of the eye, and said processing system calculates the blood vessel diameter before the detection of the nictitation and also calculates the blood vessel diameter after the detection of the nictitation.

11. A blood vessel tracking apparatus comprising:

an illumination system, having a light source and a movable mirror, for illuminating a blood vessel of an eye to be examined with light;

a sensor for receiving an image of the blood vessel illuminated with the light; and a processing system for calculating, based on an output of said sensor, a diameter of the illuminated blood vessel a plurality of times, in order to measure a change in blood vessel diameter based on the calculation, the processing system further determining the occurrence of mistracking of a blood vessel by said movable mirror when the measured change in blood vessel diameter is greater than a predetermined value.

12. An apparatus according to claim 11, further comprising a detection system for detecting a nictitation of the eye, and wherein said processing system calculates the blood vessel diameter before the detection of the nictitation and also calculated the blood vessel diameter after the detection of the nictitation.

13. A blood vessel tracking apparatus comprising;

an illumination system, having a light source and a movable mirror, for illuminating a blood vessel of an eye to be examined with light;

a sensor for receiving an image of the blood vessel illuminated with light; and a processing system for calculating, based on an output of said sensor, a diameter of the illuminated blood vessel a plurality of times, after a change of an optical path of the light effected by said movable mirror, wherein said processing system further executes processing for measuring a change in blood vessel diameter based on the calculation and for determining whether the same blood vessel has been used for calculating the blood vessel diameter based on the change in the measured blood vessel diameter.

14. A blood vessel tracking apparatus according to claims 13, wherein said processing system determines whether a single blood vessel was used by said apparatus when the change in blood vessel diameter changes by more than a predetermined amount.

15. A blood vessel tracking apparatus according to claim 13, wherein said processing system calculates a mean value for a plurality of sets of blood vessel diameters, calculates the difference between the maximum and minimum values of the mean values, and uses that difference in determining whether a single blood vessel was used by said processing system when the change in blood vessel diameter changes by more than a predetermined amount.

16. A blood vessel tracking apparatus according to claim 13, wherein said processing system determines whether the same blood vessel has been used when the difference in calculated blood vessel diameters is less than 10%.

* * * * *

UNITED STATES PATENT AND TRADEMARK OFFICE
CERTIFICATE OF CORRECTION

PATENT NO.    : 6,324,420 B1
DATED         : November 27, 2001
INVENTOR(S)   : Nobuyoshi Kishida et al.

It is certified that error appears in the above-identified patent and that said Letters Patent is hereby corrected as shown below:

Column 1,
Line 6, "a blood-" should read -- the blood- --.

Column 4,
Line 39, "path s" should read -- paths --.
Line 58, "vessel" should read -- vessels --.

Column 8,
Lines 29 and 33, "vessel s" should read -- vessels --.

Column 9,
Line 42, "vessel s" (both occurrences) should read -- vessels --.
Line 64, "vessel s" should read -- vessels --.

Column 10,
Line 49, "FIGS. 1" should read -- FIGS. 1A --.

Signed and Sealed this

Fourth Day of February, 2003

JAMES E. ROGAN
*Director of the United States Patent and Trademark Office*